United States Patent [19]

Taylor

[11] 3,990,446

[45] Nov. 9, 1976

[54] HYPODERMIC SYRINGE FOR STABILIZED ASPIRATION BY ONE HAND

[76] Inventor: Jewel Dean Randolph Taylor, 7615 Lisa Circle, Charlotte, N.C. 28215

[22] Filed: Feb. 18, 1975

[21] Appl. No.: 550,190

[52] U.S. Cl. .......................... 128/218 R; 128/218 P
[51] Int. Cl.² ........................................... A61M 5/00
[58] Field of Search ...... 128/218 P, 218 PA, 218 R, 128/218 M, 213, 214, 215, 216, 221, 272, 234, 276

[56] References Cited
UNITED STATES PATENTS

| | | | |
|---|---|---|---|
| 1,540,125 | 6/1925 | Hein | 128/218 R |
| 3,016,896 | 1/1962 | Van Sickle | 128/218 P |
| 3,336,924 | 8/1967 | Sarnoff et al. | 128/272.3 |
| 3,348,546 | 10/1967 | Roberts et al. | 128/218 M |
| 3,583,399 | 6/1971 | Ritsky | 128/218 P |
| 3,758,006 | 9/1973 | Gravlee | 128/218 P |

*Primary Examiner*—John D. Yasko

[57] ABSTRACT

A disposable hypodermic syringe for aspiration comprising a cylindrical thermoplastic barrel partially closed at one end and open at an opposite end on which two flat transverse barrel flanges extend in opposite directions to stabilize the syringe. At the partially closed end is an adaptor to facilitate connecting a needle assembly. The barrel length is approximately twice the length of the plunger and stopper coupled together and axially slideable to and fro completely within the barrel. The end of the plunger shaft opposite the stopper end consists of a flat plate with two plunger finger flanges attached thereto. Both plunger finger flanges branch perpendicularly outward from the plate through opposing apertures cut through the lateral walls of the syringe barrel. The two opposing apertures are rectangular in shape and extend from a midpoint on the barrel to a point spaced just below the largest open end. The widths of both barrel apertures align with the widths of both barrel flanges. Before aspiration the plunger stopper rests against the partially closed end of the barrel in which position the two plunger finger flanges protrude outward through the barrel apertures near the midpoint of the barrels length. Aspiration by one hand is accomplished when the plunger finger flanges are drawn toward the barrel flanges while the barrel flanges are stabilized against movement.

3 Claims, 4 Drawing Figures

HYPODERMIC SYRINGE FOR STABILIZED ASPIRATION BY ONE HAND

BRIEF SUMMARY OF THE INVENTION

This invention relates to a hypodermic syringe, and more particularly to an aspirating type hypodermic syringe that can be operated on its rearward stroke by one hand.

Often a physician, pharmacist or nurse has only one hand free with which to operate an aspirating syringe. Generally, they are stabilizing the patients limb in the case of a catheter insertion by a physician or nurse for example; or in the pharmacy environment, the pharmacist is adjusting the stopcock position in the case of an ad-mixture or compounding situation. It is due to these situations and numerous others like them that only one free hand is available with which to retract the syringe plunger rearward.

Up to now, syringes designed for one-handed operation have required the thumb to pull the syringe plunger rearward and away from the syringe barrel and fingers holding the barrel. Thus, in aspiration of fluids the thumb moved away from the hands axis and created an awkward and unstable pull against the syringe, sometimes causing patient trauma as a result of needle vibration or pistoning.

Due to the need for a smooth even aspiration or rearward stroke in several areas of application and the uniqueness of this problem, several examples are cited; for instance, during intravenous introduction of an over-the-needle catheter, one hand must aspirate the syringe to determine if the vein has been located, while the other hand stabilizes the patients arm or performs digital pressure on the vein and pushes the catheter off the hypodermic needle into the vein. In addition, another instance may be in a pharmacy situation. Here, the pharmacist may be using a syringe attached to a three-way stopcock in order to withdraw fluid from one container so as to reinject that fluid into another container for compounding an ad-mixture. By virtue of the physical effort required, the aspiration or rearward stroke of the syringe is the most difficult phase of this movement. Therefore, the need for an easier one-handed aspirating syringe is evident.

I have overcome these problems associated with thumb controlled one hand syringes by making a novel syringe with a plunger having finger flanges that slide longitudinally completely within the syringe barrel. The syringe barrel is twice the length of the syringe plunger and is designed with two opposing axial apertures out of which the plunger finger flanges protrude.

To operate the syringe for aspiration the plunger must be in the forward position with the plunger stopper resting against the partially closed end of the barrel. The thumb is then placed on the rear of the barrel flanges attached to the largest open end of the syringe barrel. The index and middle fingers are placed on the spaced finger flanges provided on the plunger and protruding out of the axial barrel apertures. The index and middle fingers are then drawn toward the thumb in order to create an aspiration or rearward stroke of the plunger. Because the primary function of this syringe is aspiration rather than injection, one handed operation is available only on the rearward or aspirating stroke of the plunger it is still necessary to use two hands to firmly inject or push forward the plunger.

This action is accomplished simply by placing the thumb and forefinger of one hand in a comfortable location alongside the graduated portion of the syringe barrel; then grasping the right or left finger flanges on the plunger with the other hand and pushing forward.

Since there is no thumb control ring on the syringe it can be quickly manipulated to perform an aspiration of blood or other fluids. In addition, the lack of the thumb ring reduces the bulk of the syringe and simplifies package size. Since the syringe can be manufactured in a one cubic centimeter graduated size syringe, it could be attached to over-the-needle catheters for quick one time use procedures, then thrown away. Because of the technique used in intravenous catheterizations, the injection or forward stroke is seldom used after the nurse or physician has found the vein with the aspiration stroke. It is this particular application that would benefit most by this syringe.

Since the syringe plunger is encased within the syringe barrel, there is no chance that the plunger could be withdrawn from the barrel accidentally. This would aid both in prevention of leakage or total loss of medicament due to complete plunger withdrawal, so often found in standard syringes available in the past. In addition, the possibility of contaminating the plunger shaft and thus possibly contaminating the medicament is reduced. Because the user need only grasp the plunger finger flanges and the fact that forty percent of the plunger shaft is encased by the syringe barrel when fully aspirated, the syringe protects the user more adequately from accidental touch contamination than standard syringes now available.

Since the syringe may be constructed so that the plunger cannot be retracted further than the last graduation mark on the syringe barrel, the fact that a user of this syringe could in effect withdraw the exact maximum capacity of the syringe and no more without error is another safety feature that should be of use in situations where a standard syringe could create an error.

A first object of this invention is to provide a hypodermic syringe that is easy to operate and stabilize with one hand while aspirating fluid with the rearward stroke of the plunger.

A second object of this invention is to provide a hypodermic syringe which can be easily grasped by the user in an operating position without having to maneuver into a thumb control ring.

Another object of this invention is to provide a hypodermic syringe for aspiration that does not require a bulky package.

Additional objects of this invention will become more obvious throughout the description of my hypodermic syringe device that follows.

BRIEF DESCRIPTION OF THE SEVERAL VIEWS OF THE DRAWING

The following views are illustrations of my invention.

Figure 1:
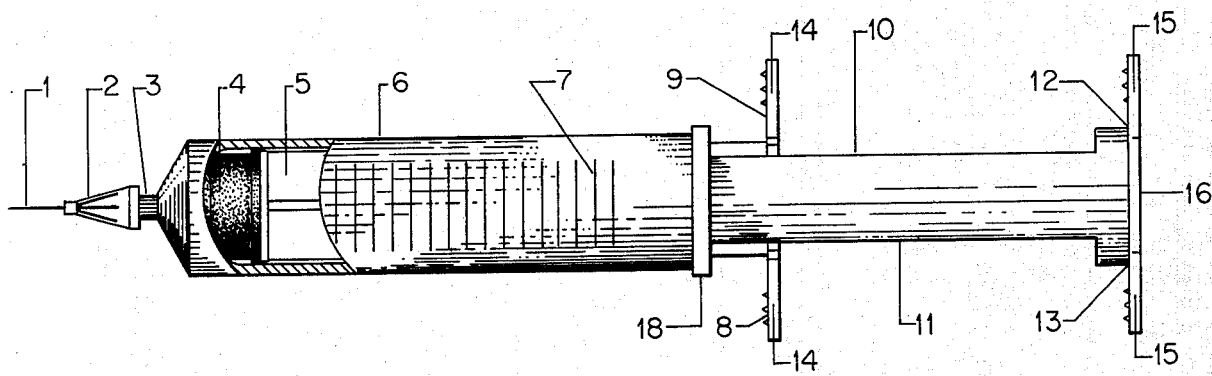
FIG. 1 is a top view partially cut away of the syringe showing the indention on the syringe profile created by the first and second barrel apertures.

Reference is made to the illustrations; this hypodermic syringe includes a barrel 6 and a needle adaptor 3 extending from the partially closed end of the barrel 6. Removeable, but for the purpose of reference and mounted on the needle adaptor is a hypodermic needle device comprising a hub 2 and needle cannula 1. Located within the syringe barrel 6 and slideable either forwardly or rearwardly is a plunger 5, the forward end of which has a resilient stopper 4 mounted thereon. The rearward end of the plunger along line 14/14 in FIG. 1 extends laterally left and right through the axial barrel apertures 10 and 11 cut through the syringe barrel 6. The lateral extentions of the plunger at line 14/14 are two spaced finger flanges 8 and 9. At the rear of the syringe barrel and attached thereon are two spaced barrel finger flanges 12 and 13 extending laterally along line 15/15 in FIG. 1. Line 14/14 and line 15/15 are both on the same plane and align with each other for all purposes. A first axial barrel aperture 10 rectangular in shape and extending longitudinally from the center of the syringe barrel at 18 to a point near the rear of the syringe barrel exists. Directly opposite the first axial barrel aperture cut through the other side of the syringe barrel is a second axial barrel aperture 11 with exactly the same dimensions as the first aperture. Within the open space formed by the two apertures 10 and 11, the plunger finger flanges 8 and 9 protrude and are longitudinally slideable forwardly and rearwardly. The two plunger finger flanges 8 and 9 are laterally spaced so that the index and middle fingers of the operator can fit on these finger flanges and in conjunction with the operators thumb resting on the center 16 of the barrel finger flanges 12 and 13 on the rear of the syringe barrel, control the rearward aspirating movement of the syringe plunger 5.

Figure 2:
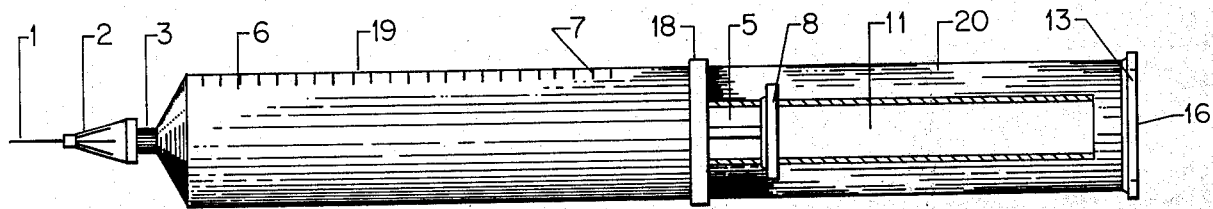
FIG. 2 is a side elevational view of the syringe showing the opening through the barrel created by the opposing axial barrel apertures.

FIG. 2, has no cut away views of the syringe 6 and more accurately shows the elevational view of the syringe 6 before aspiration of the syringe plunger 5, which would obstruct the view through the axial barrel aperture 11. In addition, it can be observed from FIG. 2 that the syringe 6 is at least twice the length of the syringe plunger 5 and that the raised circular ring 18 is located at the midpoint of the syringe length. The raised circular ring 18 divides the syringe 6 into a bottom and top barrel section 19 and 20. The graduated measurement markings 7 are located on the bottom barrel section 19.

Figure 3:
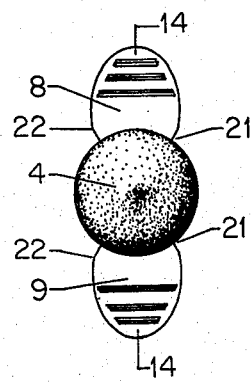
FIG. 3 is a front view of the syringe plunger showing the shape of the finger flanges.
Figure 4:
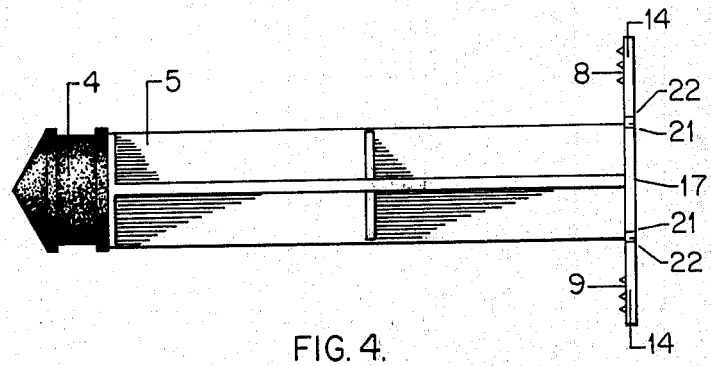
FIG. 4 is a cross-sectional view of the syringe plunger showing the cross-section view of the finger flanges taken along line 14/14 of FIG. 3.

A more detailed description of the syringe plunger finger flanges will be made with reference to FIGS. 3 and 4. Both plunger finger flanges have substantially the same shape and for illustrative purposes the front view of the plunger finger flanges from the stopper 4 have been shown along line 14/14 in detail in FIG. 3.

The finger flanges 8 and 9 on the plunger are designed so that the width across the neck 21 of each flange has a measured distance fractionally less than the width of either of the axial barrel apertures 10 and 11 so that the plunger flanges are freely slideable forwardly and rearwardly within the apertures. Connecting these two finger flanges 8 and 9 is a plate 17 with a diameter that is fractionally less than the diameter of the plunger stopper 4. The plate 17 is molded to the rear of the plunger shaft 5.

The plunger finger flanges 8 and 9 are formed as flat extensions of the plate beginning at the neck 21 and expanding to a maximum width at the midpoint 22 and then returning to the same width as the neck at the distal ends. As can be seen from FIG. 3, the plunger finger flanges 8 and 9 each provide a relatively large, flat face which the fingers can easily engage for smooth aspiration of the syringe plunger.

The barrel finger flanges 12 and 13 at the rear of the syringe barrel along line 15/15 should be designed to be comfortable for both the thumb to rest alone, or the thumb and the middle and index finger of the same hand to be able to grasp and hold the syringe if required. The design of flanges 12 and 13 could follow the design of flanges 8 and 9 on the syringe plunger 5 as shown in FIG. 3, or it could utilize a simple oval configuration consistent with the design of syringe flanges available on standard hypodermic syringes now manufactured.

The flanges 12 and 13 at the rear of the syringe however should be molded integrally with the top barrel section 20 for simplicity of assembly with the other parts of the syringe.

In syringe sizes larger than ten cubic centimeters, the raised circular ring 18 may be molded separately and then attached to the bottom barrel section 19 by either spin welding, or cementing or some other similar means. The bottom barrel section 19 can be injection molded or formed by some other similar means. The top barrel section 20 can be formed similar to the bottom barrel and the axial barrel apertures 10 and 11 can be die cut or molded, or by some other similar means formed through the lateral walls of the top barrel section.

The assembly of the larger syringe sizes should start with the molding and complete assembly of the syringe plunger 5, the plunger finger flanges 8 and 9 and the plunger stopper 4. The circular ring 18 should be pre-attached to the bottom syringe barrel section 19 prior to inserting the completed syringe plunger 5. Next, the completed syringe plunger 5 should be placed into the shaft of the bottom barrel section 19 before connecting the bottom 19 and top 20 barrel sections together. Then the top barrel section 20 should be aligned so that the left and right axial barrel apertures 10 and 11 align over the left and right finger flanges of the syringe plunger 8 and 9. Following this step, the bottom and top barrel sections 19 and 20 should be spin welded or cemented at the raised circular ring 18.

In syringe sizes smaller than ten cubic centimeters, the raised circular ring 18 is unnecessary for constructing the syringe. The bottom barrel section 19 and the top barrel section 20 can be formed as one unit by injection molding the entire syringe barrel as one part and either die cutting or integrally molding the two axial barrel apertures 10 and 11 through the lateral walls of the top portion of the syringe barrel.

The assembly of the smaller syringe sizes should start with the molding of the syringe plunger 5 and the plunger finger flanges 8 and 9. Next, the molding of the syringe barrel 6, and two axial apertures 10 and 11, and the barrel flanges 12 and 13 should be completed. Following these steps the plunger stopper 4 should be inserted through the first or second axial barrel aperture and moved down inside the barrel toward the partially closed end of the barrel 3. To complete the assembly, the syringe plunger 5 should then be forced into the barrel shaft through the first or second axial barrel aperture and made to lock with the plunger stopper 4 so that the plunger finger flanges 8 and 9 are extending left and right out of the axial barrel apertures 10 and 11.

I have illustrated and described a preferred approach to the embodiment of my invention. However, artisans skilled in the medical device industry will understand that certain modifications may be made to this embodiment without departing from the integrity, uniqueness, and the scope of my invention.

I claim:

1. A disposable hypodermic syringe for stabilized aspiration by one hand of fluids comprising:
   a. a cylindrical thermoplastic barrel open at one end and partially closed at an opposite end with a substantially constant diameter bore extending between its two ends, the partially closed end tip of the barrel having an adaptor for supporting a needle assembly;
   b. a bottom barrel section and a top barrel section either welded or molded together to form the complete syringe barrel whose length is approximately twice the length of the syringe plunger and stopper coupled together and axially slideable to and fro completely within said syringe barrel, said stopper being in fluid tight contact with the inside walls of said barrel;
   c. a first, axial barrel aperture rectangular in shape and beginning at a midpoint on the syringe barrel between the tip and the open opposite end, its shortest sides perpendicular to the barrel axis, its longest sides parallel to the barrel axis, said apertures length beginning from said barrel midpoint and extending to a point spaced just below the largest open end of said barrel, said apertures width extending around the circumference of the barrel to a point fractionally short of meeting the opposing barrel aperture: and
   d. a second, axial barrel aperture rectangular in shape and beginning at a midpoint on the syringe barrel between the tip and the open opposite end, its shortest sides perpendicular to the barrel axis, said apertures length beginning from said barrel midpoint and extending to a point spaced just below the largest open end of said barrel, said apertures width extending around the circumference of the barrel to a point fractionally short of meeting the opposing barrel aperture, whereby said first and second axial barrel apertures stabilize the lateral movement of said plunger flanges and control the volume capacity of said syringe barrel by limiting the vertical distance that said syringe plunger can be withdrawn;
   e. a flat, circular thermoplastic plate attached to the end of the plunger shaft opposite said stopper, said flat circular thermoplastic plate having two opposing thermoplastic flanges extending through the first and second axial barrel apertures, said two opposing thermoplastic flanges providing finger grips with which to manipulate said plunger and stopper toward and away from the partially closed tip end of said syringe barrel;
   f. a pair of flat, transverse thermoplastic barrel flanges adjacent to the large open end of said syringe barrel and integrally molded to and oppositely extending outward from said top barrel section, said barrel flanges being aligned to a midpoint in the width of the two opposing barrel apertures and therefore on the same plane as the two syringe plunger flanges protruding outward therefrom, said barrel flanges being a means for holding the barrel firm with the thumb while the index and middle fingers of that same hand grip said plunger flanges and draw said plunger away from the partially closed end tip of said barrel creating negative pressure within said barrel, said barrel flanges in conjunction with said plunger flanges thereby providing a syringe which offers one handed operation while performing aspiration.

2. A disposable hypodermic syringe for stabilized aspiration by one hand of fluids according to claim 1 wherein:
   a. a first, thermoplastic plunger flange branching at its neck outward from the flat circular plate on said plunger through the opening created by the first axial barrel aperture in a manner so that the neck of said plunger flange does not touch the sides of said aperture, the width at the midpoint between the flange neck at the plunger plate and the distal end of said flange being a distance equal to half the diameter through said syringe barrel, the length of said plunger flange from the neck to the distal end being a distance equal to the diameter through said syringe barrel; and
   b. a second, thermoplastic plunger flange branching at its neck outward from the flat circular plate on said plunger through the opening created by the second axial barrel aperture in a manner so that the neck of said plunger flange does not touch the sides of said aperture, the width at the midpoint between the flange neck at the plunger plate and the distal end of said flange being a distance equal to half the diameter through said syringe barrel, the length of said plunger flange from neck to distal end being a distance equal to the diameter through said syringe barrel, providing in conjunction with the first plunger flange a finger gripping area that is proportionate to the size of the syringe being used, thereby incorporating a means for easily grasping said syringe in an aspirating manner.

3. A disposable hypodermic syringe for stabilized aspiration by one hand of fluids according to claim 1 wherein the size of each thermoplastic barrel flange is the same size as that size described for said first and said second plunger flanges providing a syringe of uniform dimensions that does not require a bulky package.

* * * * *